United States Patent [19]

Nita et al.

[11] Patent Number: 5,427,118
[45] Date of Patent: Jun. 27, 1995

[54] ULTRASONIC GUIDEWIRE

[75] Inventors: Henry Nita; Douglas H. Gesswein; John H. Wang, all of Mission Viejo; Timothy C. Mills, Newport Beach, all of Calif.

[73] Assignee: Baxter International Inc., Deerfield, Ill.

[21] Appl. No.: 131,793

[22] Filed: Oct. 4, 1993

[51] Int. Cl.⁶ ............................................. A61B 5/00
[52] U.S. Cl. ................................... 128/772; 601/2
[58] Field of Search ............... 128/657, 772, 24 A, 128/660; 604/22; 601/2-4

[56] References Cited

U.S. PATENT DOCUMENTS

| | | |
|---|---|---|
| 3,352,303 | 11/1967 | Delaney . |
| 3,433,226 | 3/1969 | Boyd . |
| 3,526,219 | 9/1970 | Balamuth . |
| 3,565,062 | 3/1971 | Kuris . |
| 3,589,363 | 6/1971 | Banko . |
| 3,618,594 | 11/1970 | Banko . |
| 3,809,093 | 5/1974 | Abraham . |
| 3,823,717 | 7/1974 | Pohlman . |
| 3,861,391 | 1/1975 | Antonevich et al. . |
| 3,896,811 | 7/1975 | Storz . |
| 4,188,952 | 2/1980 | Loschivlov et al. . |
| 4,214,586 | 7/1980 | Mericle . |
| 4,223,676 | 9/1980 | Wuchinich et al. ............... 128/276 |
| 4,337,090 | 6/1982 | Harrison .......................... 148/402 |
| 4,366,819 | 1/1983 | Kaster . |
| 4,431,006 | 2/1984 | Trimmer et al. ................. 128/660 |
| 4,474,180 | 10/1984 | Angulo ............................. 128/328 |
| 4,505,767 | 3/1985 | Quin ................................. 148/402 |
| 4,565,589 | 1/1986 | Harrison .......................... 148/402 |
| 4,587,958 | 5/1986 | Noguchi et al. ................. 128/24 A |
| 4,587,972 | 5/1986 | Morantte ......................... 128/660 |
| 4,589,419 | 5/1986 | Laughlin et al. ................ 128/663 |
| 4,665,906 | 5/1987 | Jervis . |
| 4,692,139 | 9/1987 | Stiles ................................ 604/22 |
| 4,741,731 | 5/1988 | Starck et al. .................... 604/22 |
| 4,750,902 | 6/1988 | Wuchinich et al. ............. 604/22 |
| 4,764,165 | 8/1988 | Reimels et al. ................. 604/35 |
| 4,794,931 | 1/1989 | Yock ................................. 128/660.03 |
| 4,799,496 | 1/1989 | Hargraves ........................ 128/772 |
| 4,800,876 | 1/1989 | Fox et al. . |
| 4,808,153 | 2/1989 | Parisi . |
| 4,811,743 | 3/1989 | Stevens ............................ 128/657 |
| 4,821,731 | 4/1989 | Martinelli et al. .............. 128/662.06 |
| 4,841,977 | 6/1989 | Griffith . |
| 4,844,092 | 7/1989 | Rydell ............................. 128/772 |
| 4,867,141 | 9/1989 | Nakada ........................... 128/24 A |
| 4,870,953 | 10/1989 | DonMichael .................... 128/24 A |
| 4,898,575 | 2/1990 | Fischell et al. .................. 604/22 |
| 4,917,097 | 4/1990 | Proudian et al. ................ 128/662.06 |
| 4,919,133 | 4/1990 | Chiang ............................ 606/159 |
| 4,920,954 | 5/1990 | Alliger et al. ................... 128/24 A |
| 4,923,441 | 5/1990 | Shuler ............................. 604/22 |
| 4,924,863 | 5/1990 | Sterzer ............................ 606/27 |

(List continued on next page.)

FOREIGN PATENT DOCUMENTS

| | | |
|---|---|---|
| 0424231 | 4/1984 | European Pat. Off. . |
| 189329 | 7/1986 | European Pat. Off. . |
| 293472 | 11/1986 | European Pat. Off. . |
| 208175 | 1/1987 | European Pat. Off. . |
| 0209468 | 1/1987 | European Pat. Off. . |
| 234951 | 2/1987 | European Pat. Off. . |
| 316796 | 11/1988 | European Pat. Off. . |

(List continued on next page.)

OTHER PUBLICATIONS

Circulation, vol. 81, No. 2, Feb. 1990, "Application of a New Phased-Array Ultrasound Imaging Catheter in the Assessment of Vascular Dimensions," pp. 660–666.

Primary Examiner—Max Hindenburg
Attorney, Agent, or Firm—Stetina Brunda Buyan; Raymond Sun

[57] ABSTRACT

An ultrasonic guidewire insertable into a mammalian body for purposes of guiding a medical catheter, scope or other medical device into the body and, additionally, connectable to an external ultrasound generating source to transmit ultrasonic energy into the body. The invention includes methods of using the ultrasonic guidewire for purposes of ablating obstructive matter in a blood vessel or other body cavity and/or for delivering ultrasonic energy to treat vasospasm or muscular spasms within the body.

24 Claims, 5 Drawing Sheets

U.S. PATENT DOCUMENTS

| | | | |
|---|---|---|---|
| 4,936,281 | 6/1990 | Stasz | 128/660.03 |
| 4,957,111 | 9/1990 | Millar | 128/662.06 |
| 4,960,411 | 10/1990 | Buchbinder | 604/95 |
| 4,966,583 | 10/1990 | Debbas | 604/98 |
| 4,967,653 | 11/1990 | Hinz | 100/168 |
| 4,967,753 | 11/1990 | Haase et al. | 128/772 |
| 4,979,939 | 12/1990 | Shiber | 606/159 |
| 4,988,356 | 1/1991 | Crittenden | 606/192 |
| 4,989,583 | 2/1991 | Hood | 128/24 A |
| 4,998,527 | 3/1991 | Meyer | 128/6 |
| 5,022,399 | 6/1991 | Biegeleisen | 128/662.06 |
| 5,029,588 | 7/1991 | Yock et al. | 128/662.06 |
| 5,058,570 | 10/1991 | Idemoto et al. | 128/24 AA |
| 5,061,238 | 10/1991 | Shuler | 604/22 |
| 5,069,664 | 12/1991 | Guess et al. | 604/22 |
| 5,076,276 | 12/1991 | Sakurai et al. | 128/24 AA |
| 5,100,423 | 3/1992 | Fearnot | 606/159 |
| 5,151,085 | 9/1992 | Sakurai et al. | 604/22 |
| 5,163,421 | 11/1992 | Bernstein | 128/24.1 |
| 5,188,589 | 2/1993 | Wypych et al. | 604/22 |
| 5,199,943 | 4/1993 | Wypych | 604/22 |
| 5,211,625 | 5/1993 | Sakurai | 604/22 |
| 5,242,385 | 9/1993 | Strukel | 604/22 |
| 5,248,296 | 9/1993 | Alliger | 128/24 AA |
| 5,255,669 | 10/1993 | Kubota et al. | 128/24 AA |
| 5,261,877 | 11/1993 | Fine | 604/96 |
| 5,269,297 | 12/1993 | Weng et al. | 128/24 AA |
| 5,312,328 | 5/1994 | Nita et al. | 604/22 |

FOREIGN PATENT DOCUMENTS

| | | |
|---|---|---|
| 347098 | 6/1989 | European Pat. Off. |
| 315290 | 10/1989 | European Pat. Off. |
| 443256 | 12/1990 | European Pat. Off. |
| 472368 | 2/1992 | European Pat. Off. |
| 2424733 | 11/1980 | France |
| 2641693 | 7/1990 | France |
| 2643272 | 8/1990 | France |
| 2438648 | 2/1976 | Germany |
| 2541919 | 3/1977 | Germany |
| 2703486 | 12/1977 | Germany |
| 3726210 | 8/1987 | Germany |
| 3707567 | 9/1987 | Germany |
| 3707921 | 9/1987 | Germany |
| 1520448 | 7/1975 | United Kingdom |
| 2212267 | 7/1989 | United Kingdom |
| WO87/01276 | 3/1987 | WIPO |
| WO87/05793 | 10/1987 | WIPO |
| WO89/05123 | 6/1989 | WIPO |
| WO89/06515 | 7/1989 | WIPO |
| WO89/07419 | 8/1989 | WIPO |
| WO90/01300 | 2/1990 | WIPO |
| WO90/07303 | 7/1990 | WIPO |
| WO91/02489 | 3/1991 | WIPO |
| WO91/14401 | 10/1991 | WIPO |
| WO92/10140 | 6/1992 | WIPO |
| WO92/11815 | 7/1992 | WIPO |
| WO92/15253 | 9/1992 | WIPO |

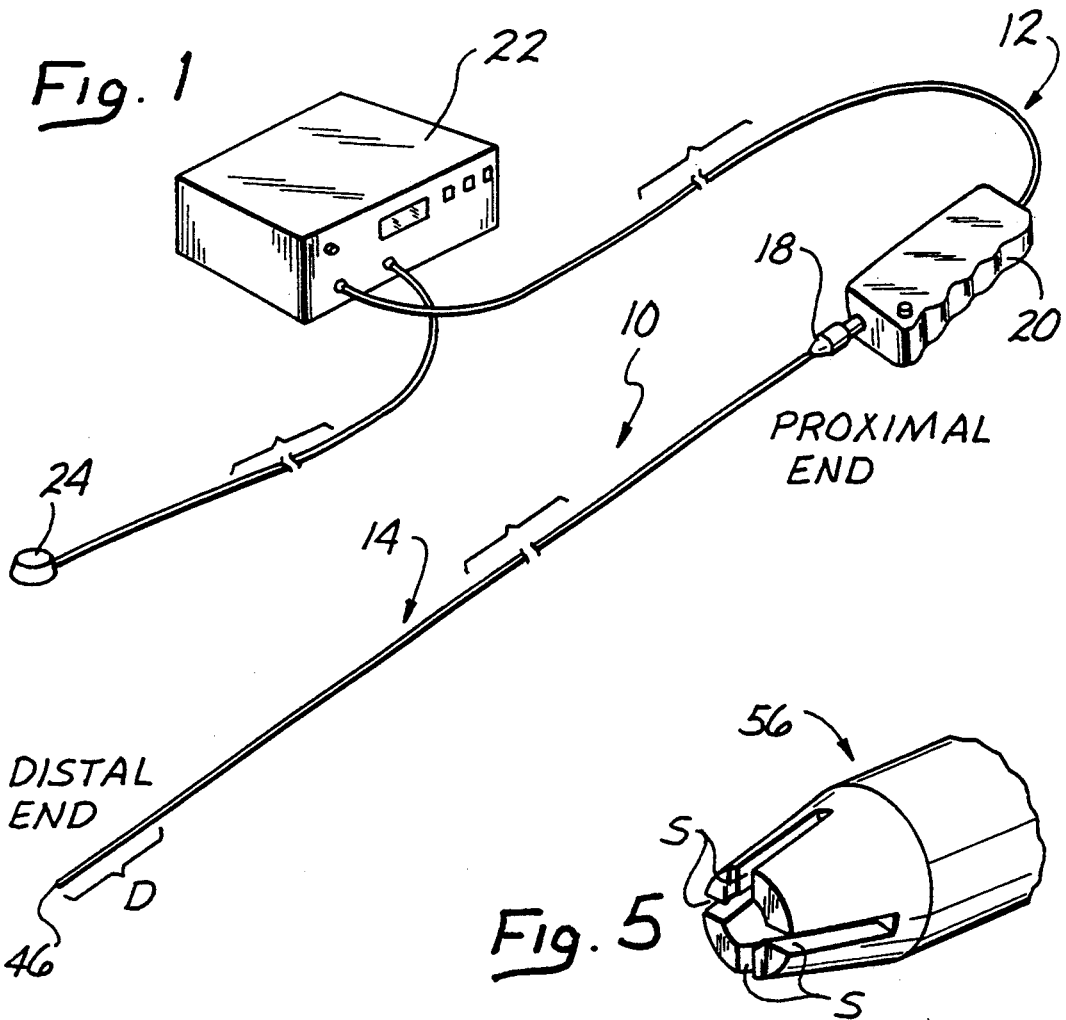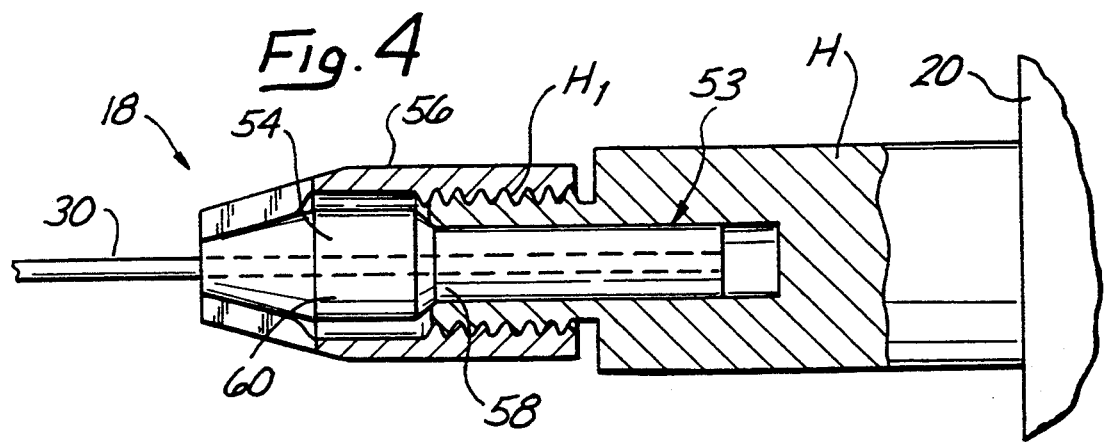

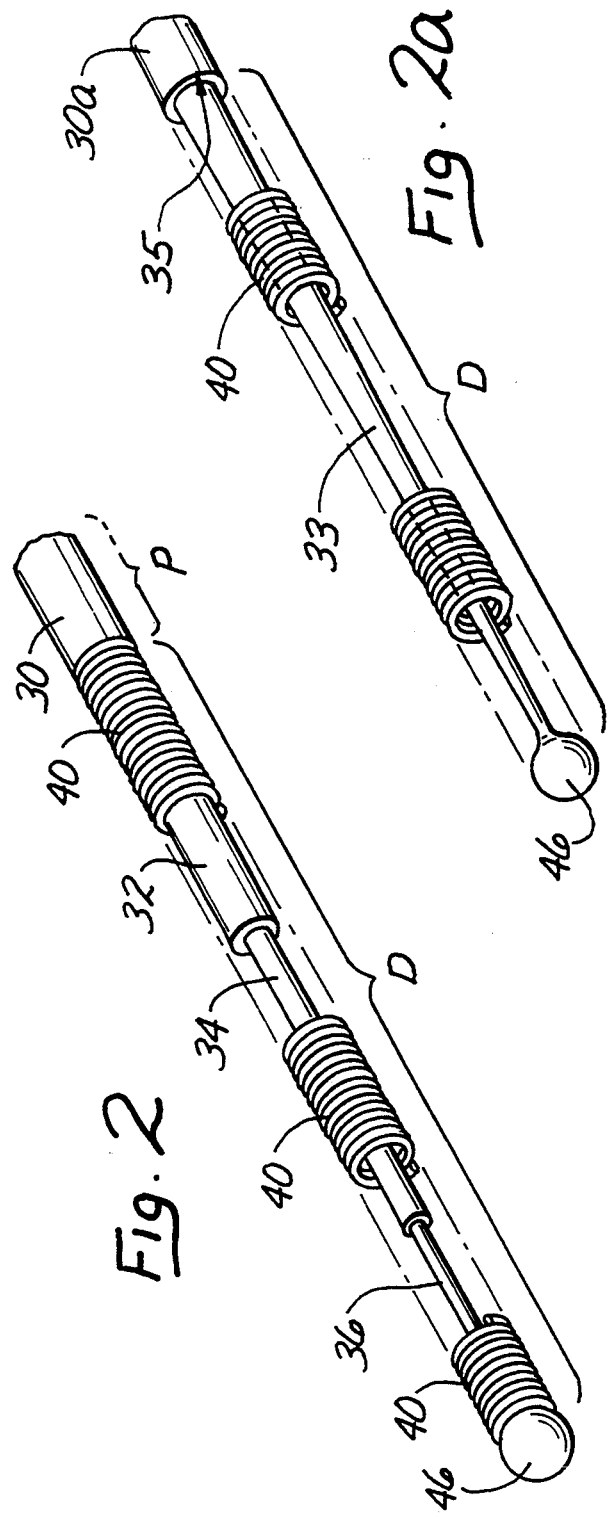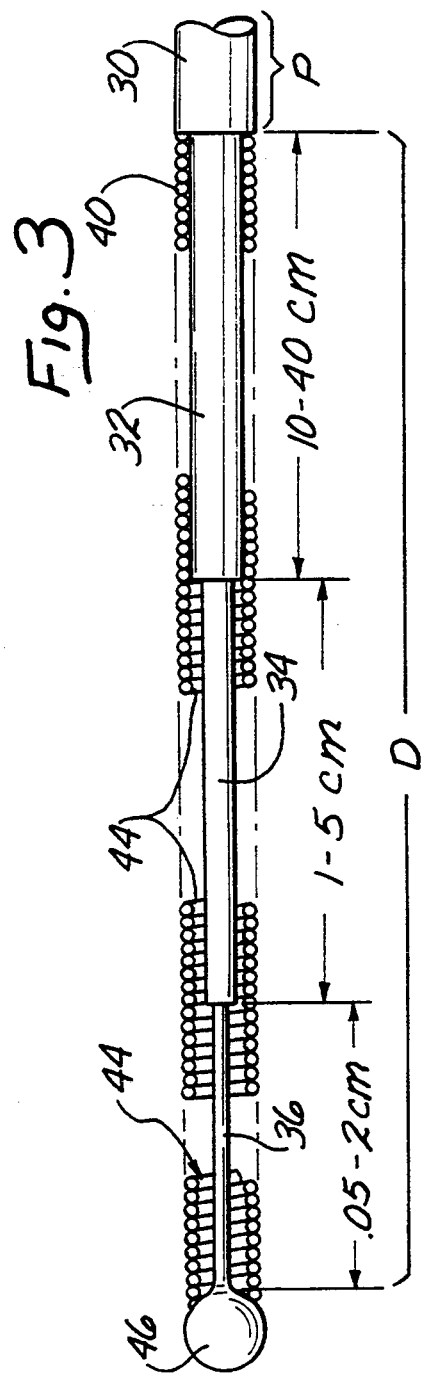

ULTRASONIC GUIDEWIRE

FIELD OF THE INVENTION

The present invention pertains generally to medical devices and more particularly to an ultrasonic guidewire useable to guide the placement of tubular catheters, scopes and other medical devices and, additionally, capable of transmitting ultrasonic energy to effect ultrasonic treatment (e.g., ablation) of target matter (e.g., obstructions) in the body cavity or passageway into which the guidewire is inserted.

BACKGROUND OF THE INVENTION

Many medical procedures utilize elongate flexible guidewires for guiding the insertion of catheters, scopes or other instruments into ducts, passageways, vessels or cavities of the body.

In particular, certain diagnostic and/or interventional cardiovascular procedures (e.g., cardiac catheterization, percutaneous transluminal coronary angioplasty, etc....) utilize guidewires to facilitate the insertion and advancement of catheters to specific locations within the cardiac and/or vascular anatomy. It is the usual practice, in such cardiovascular procedures, to, percutaneously insert the guidewire, through an introducer, into a peripheral blood vessel. The guidewire is then advanced to a point where the distal end of the guidewire is positioned at or near a target lesion or anatomical structure. Thereafter, a selected catheter or instrument is advanced over the pre-positioned guidewire to the desired treatment location.

Also, in some gastroenterologic procedures, guidewires are utilized to guide the advancements of catheters, endoscopes or other instruments through various portions of the gastrointestinal tract or biliary tree. For example, one gastroenterologic procedure, known as Endoscopic Retrograde Cholangiopancreatography (ERCP), a duodenoscope is inserted transesophogeally and advanced into the duodenum. The duodenoscope is then utilized to visually locate an opening, known as the ampulla of Vater, through which the Common Bile Duct enters the gastrointestinal tract. A guidewire is then passed through a working channel of the duodenoscope, and into the ampulla. The guidewire is then advanced through the Common Bile Duct into the Pancreatic Duct. With the guidewire positioned in the Pancreatic Duct, a small catheter is then advanced over the guidewire and into the Pancreatic Duct, whereat such catheter may be used to inject radiopaque dye and/or for collecting pancreatic secretions for cytological analysis.

Other types of medical procedures which utilize guidewires include various urological and gynecological procedures wherein it is desirable to pass a flexible scope, catheter or other instrument over a prepositioned guidewire to a target location within a duct, organ or anatomical passageway of the body.

At least some of the guidewires utilized in medical procedures are formed of a longitudinal wire core having a continuous coil of thin steel wire tightly wound thereabout. Such guidewires typically have an outer diameter of less than 0.1 inches and, in many instances, approximately 0.008-0.040 inches. The coiled outer surface of the guidewire may be covered with a smooth, physiologically inert coating such as a fluorocarbon (e.g., Teflon TM E. I. Dupont de Neumours Corp., Wilmington, Del.) or silicone (e.g., MTX Coating, Dow Corning, Midland, Mich.).

Advancement of a guidewire to a desired location within a passageway or vessel may be difficult or impossible in cases where there exists a total or near-total blockage of the passageway or vessel. For example, in percutaneous transluminal coronary angioplasty (PTCA) procedures, the presence of a complete occlusion within the lumen of a diseased coronary artery may prevent the tip of a guidewire from being advanced through such occlusive lesion such that an angioplasty catheter may subsequently be advanced to a proper operative location adjacent the occlusive lesion. In such instances, the inability to advance the guidewire through the fully occluded coronary vessel may necessitate abandonment of the PTCA procedure and/or the election of an alternative, more invasive, procedure such as cardio-thoracic surgery. Thus, it would be highly desirable to develop a guidewire which is capable of safely boring or creating a tunnel or passageway through a total or near-total occlusion.

Another problem which may be encountered during guidewire assisted cardiovascular procedures (e.g., PTCA) is the occurrence of vasospasm or involuntary contraction of the blood vessel into which the guidewire has been inserted. The occurrence of such spasm or contraction may necessitate the administration of vasospasm relaxing pharmacologic agents. The occurrence of such blood vessel spasm may severely compromise the hemodynamic function of the blood vessel, with potentially serious secondary effects (e.g., infarction of tissue due to disruption of blood supply). Thus, it would be highly desirable to develop a guidewire capable of delivering a non-pharmacologic vasorelaxant treatment directly to the blood vessel. One type of non-pharmacologic, vasorelaxant treatment which may be utilized for this purpose is the delivery of ultrasonic vibration to the blood vessel wall. See, Chokahi, S. K., et al., *Ultrasonic Energy Produces Endotheliel Dependent Vasomotor Relaxation In Vitro,* (Abstract) 62nd Scientific Sessions, American Heart Association (1989); Fischell, T. A., et al., *Ultrasonic Energy: Effects on vascular Function and Integrity; Circulation;* 84:1783-1795 (1991)

One prior ultrasound-transmitting wire is disclosed in U.S. Pat. No. 5,156,143 (Bocquet, et al.) entitled ULTRASONIC PERCUSSION DEVICE.

The device disclosed in U.S. Pat. No. 5,156,143 comprises an elongate wire member of constant diameter which is purportedly insertable into a blood vessel to transmit ultrasonic energy from an extracorporeally located ultrasound generating device, to a location within the blood vessel. The ultrasonic vibrations at the distal end of the device are purportedly capable of destroying obstructive material (i.e. atheromata) within a blood vessel by way of ultrasonic percussion.

There exists a need in the art for the invention and development of improved ultrasonic guidewires capable of transmitting ultrasonic energy from an ultrasound generation device located outside the body to a site within the body for purposes of a) ablating, boring or through an existing mass of obstructive matter and/or b) reversing or preventing untoward spastic or constrictive activity in at least some anatomical ducts, passageways and vessels of the body.

SUMMARY OF THE INVENTION

The present invention provides an ultrasonic guidewire device comprising an elongate, ultrasound transmitting guidewire which if useable to guide medical catheters, scopes and other devices into the body and, also, may be connected to an external ultrasound source to transmit ultrasonic energy into the body.

In accordance with an embodiment of the invention, the device comprises an elongate guidewire body having a proximal portion and a distal portion. The proximal portion of the guidewire body may be formed of an elongate wire member preferably having a length of approximately 20-150 cm and an outer diameter of approximately 0.008-0.040 mm. The distal portion of the guidewire body comprises one or more distal wire segment(s) which is/are smaller in diameter or cross-sectional dimension than the elongate proximal portion of the guidewire body. The distal wire segment(s) extend forward of the distal end of the proximal wire member and may be formed by machining (i.e., turning down) of the distal portion of the proximal wire member. A helically wound wire coil is disposed about the outer surface at least one distal wire core member. Preferably, the outer diameter of the helically wound wire coil is approximately the same as the outer diameter of the elongate wire member which forms the proximal portion of the guidewire body, thereby forming a flush, substantially even outer surface over the entire length of the guidewire device.

A bulbous tip member may be positioned or formed on the distal end of the guidewire body. Such bulbous tip member may be formed by concomitantly melting the distal end of the outer wire coil and the distal end of the distal core member, thereby causing such materials to become fused and to form the desired bulbous distal tip member.

In one preferred embodiment of the invention, the distal wire segment(s) comprise three (3) progressively smaller distal wire segment(s), extending in the proximal direction from the proximal end of the elongate proximal portion of the guidewire device. Said three (3) progressively smaller distal core members are surrounded by a continuous constant-diameter helically wound outer wire coil.

In another preferred embodiment of the invention, the said distal wire segment(s) comprise a single distal wire segment having a gradually tapered diameter cross-sectional dimension.

Further in accordance with the invention, there is provided a proximal connector assembly positionable on the proximal end of the guidewire device to facilitate the connection thereof to an ultrasound generating transducer or other ultrasound source. Such proximal connector apparatus is preferably removable from the proximal end of the guidewire, without the use of tools, so as to permit periodic passage of catheters, scopes and/or other instruments over the body of the guidewire in accordance with common clinical practice.

Further in accordance with the invention, there are provided methods for utilizing an ultrasonic guidewire device to remove, ablate or otherwise treat various obstructive disorders of the mammalian blood vessels and/or other anatomical passageways of the mammalian body. In particular, the present invention includes a method for utilizing an ultrasonic guidewire to bore a pilot hole or passageway through a total or near-total obstruction within a blood vessel or other anatomical passage. Such pilot hole or passageway created by the ultrasonic guidewire may subsequently be utilized for passage of a secondary treatment apparatus (e.g., a balloon dilation catheter) into the occlusive lesion to effect ablation, removal, compression or dilation of the lesion and/or therapeutic intervention aimed at restoring full or partial patency to the occluded blood vessel or anatomical passage.

Further objects and advantages of the invention will become apparent to those skilled in the art upon reading and understanding of the following detail description, examples and accompanying drawings.

BRIEF DESCRIPTION OF THE DRAWINGS

FIG. 1 is a perspective view of an ultrasonic guidewire of the present invention operatively connected to an ultrasound generating system.

FIG. 2 is a partially cut-away perspective view of the distal portion of a first embodiment of an ultrasonic guidewire of the present invention.

FIG. 2a is a partially cut-a-way perspective view of the distal portion of a second embodiment of an ultrasonic guidewire of the present invention.

FIG. 3 is a partially cut-away side elevational view of the distal portion of an ultrasonic guidewire of the present invention.

FIG. 4 is a longitudinal sectional view of a proximal coupling apparatus whereby the ultrasonic guidewire of the present invention may be coupled to an ultrasound generating system.

FIG. 5 is a perspective view of a gripping ferrule component of the proximal connector assembly shown in FIG. 4.

DETAILED DESCRIPTION OF PREFERRED EMBODIMENTS

Figure 6A:
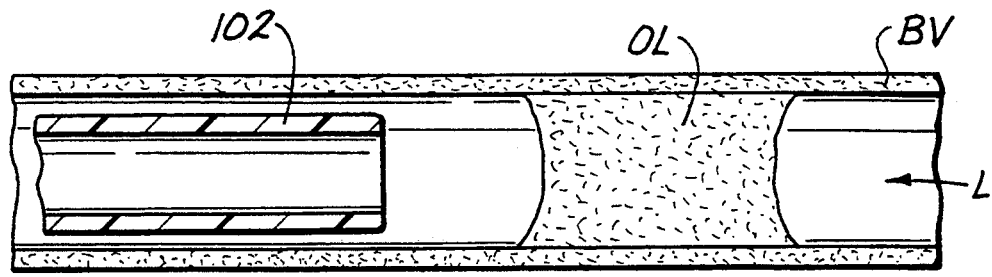
FIG. 6a-g is a step-wise illustration of an angioplasty procedure wherein an ultrasonic guidewire of the present invention is utilized to initially bore or shield a passageway through a total or near-total obstruction within a vessel and to subsequently guide the operative placement of an angioplasty apparatus (e.g., a balloon catheter) within the obstructive matter.
Figure 6B:
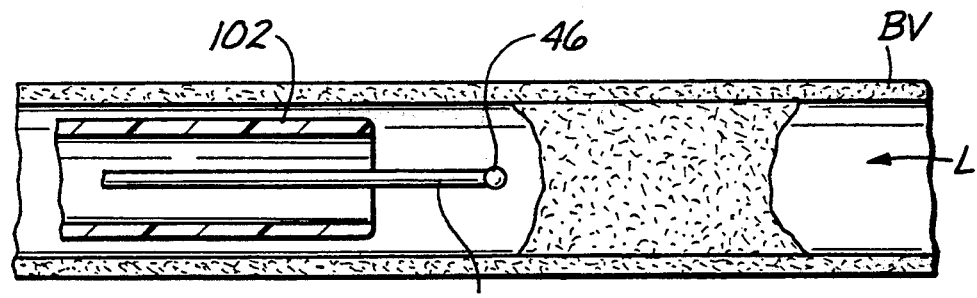
Figure 6C:
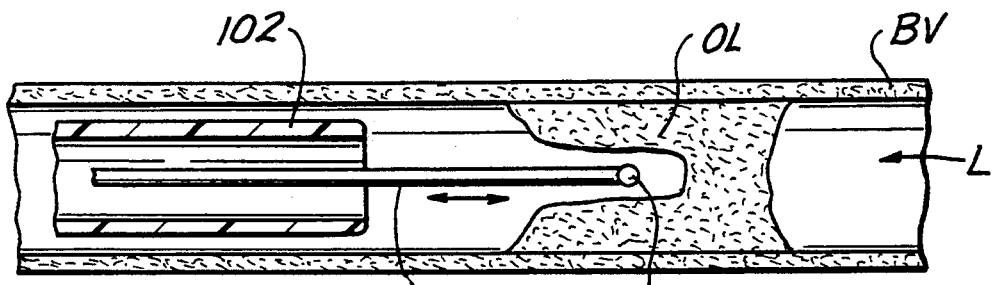
Figure 6D:
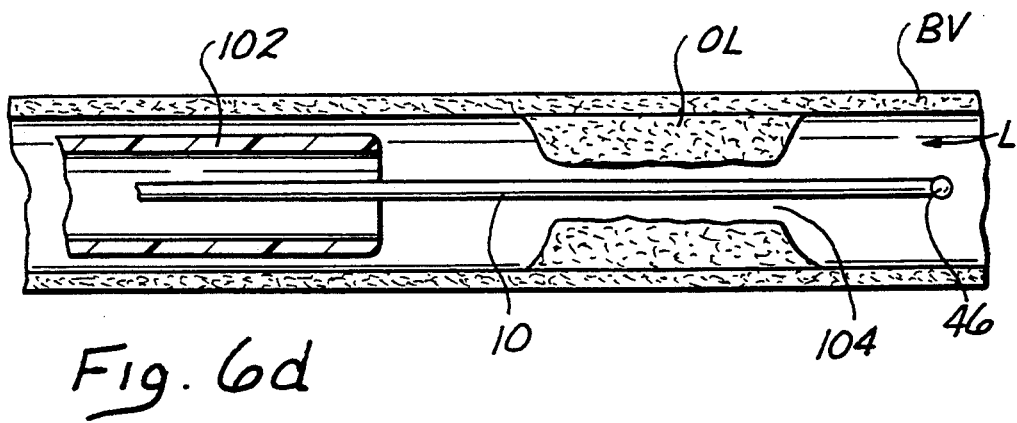
Figure 6E:
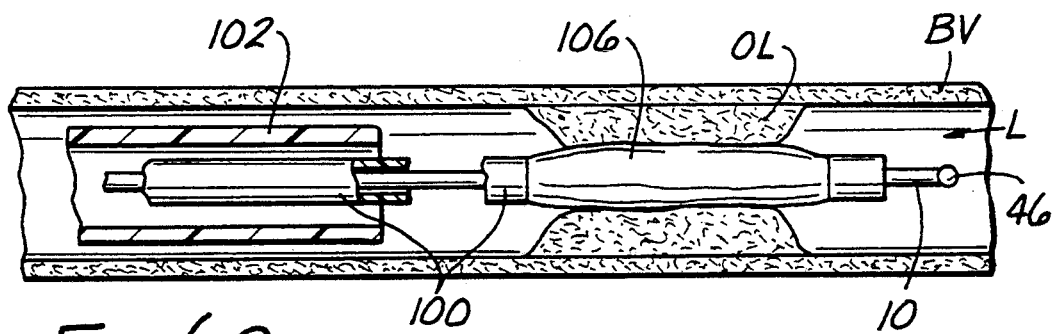
Figure 6F:
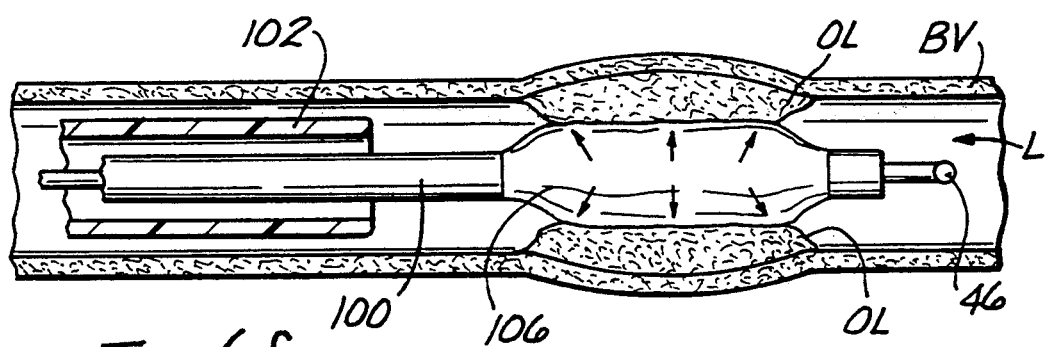
Figure 6G:
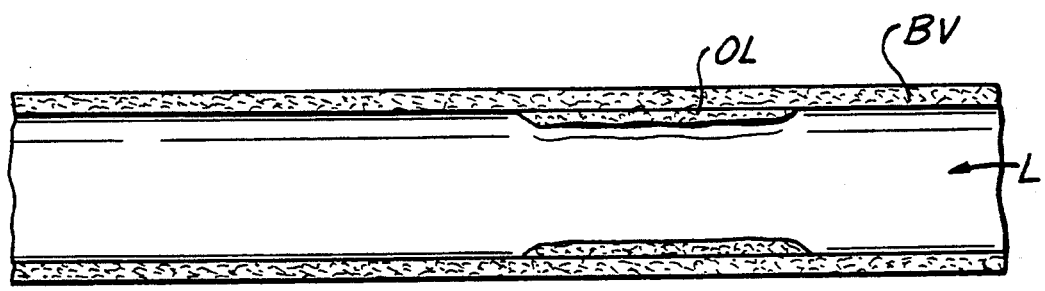

The following detailed description and the accompanying drawings are provided for purposes of describing and illustrating presently preferred embodiments of the invention only, and are not intended to limit the scope of the invention in any way.

A PREFERRED ULTRASONIC GUIDEWIRE DEVICE

With reference to the drawings, FIG. 1 shows, in perspective view, an ultrasonic guidewire device 10 of the present invention operatively connected to a separate ultrasound generating system 12.

The preferred ultrasonic guidewire device 10 generally comprises an elongate guidewire body 14 having a blunt or bulbous distal tip 46. A proximal ultrasound connector assembly 18 is positioned on the proximal end of the guidewire body 14 to facilitate connection or coupling of the guidewire device 10 to an ultrasound generating system 12.

The ultrasound generating system shown in FIG. 1 comprises a hand-held ultrasound transducer 20 (e.g., Model UAT-1000 Baxter Healthcare Corporation, Edwards Less Invasive Surgery Division, 17221 Redhill Avenue, Irvine, Calif. 92714) connected to a signal generator 24 (e.g., UAG-1110 Baxter Healthcare Corporation, Edwards Less Invasive Surgery Division, 17221 Redhill Avenue, Irvine, Calif. 92714). The signal generator 22 is provided with a foot actuated on-off switch 24. When depressed, the foot actuated on-off switch 24 causes the signal generator 22 to send an electrical signal to the ultrasound transducer 20. The ultrasound transducer 20 then converts the electrical signal to ultrasonic energy. The ultrasonic energy emanating from the transducer 20 then passes into the proximal end of the guidewire body 14 by way of proximal connector assembly 18. The ultrasonic energy is transmitted, in the distal direction, through the ultrasonic guidewire body 14 to the distal tip 46 thereof.

As shown in the embodiment of FIGS. 2 and 3 the guidewire body 14 of the device 10 comprises a proximal portion P, typically 20-150 centimeters in length, and a distal portion D, typically 10-40 centimeters in length. The proximal portion P of the guidewire body 14 preferably comprises a solid elongate proximal wire segment 30 formed of metal wire material such as nickel-titanium alloy (e.g., Tinel TM, Raychem Corporation, Menlo Park, Calif.) or stainless steel. The distal portion D of the guidewire 10 is formed of distal wire segments comprising progressively smaller diameter turned down regions on the distal end of the proximal wire segment 30. Such first, second and third distal wire segments 32, 34, and 36 are surrounded by and extend longitudinally through the bore 44 of, a tightly wound outer coil 40.

The first 32, second 34 and third 36 distal wire segments are preferably co-axial with the proximal wire segment 30 and are formed by machining (i.e., turning down) of the distal portion of the proximal wire segment 30, so as to form three progressively smaller stepped down distal segments, as shown. In the embodiment shown in FIG. 2, the diameter of the first distal wire segment 32 is approximately 0.2-0.3 mm. The diameter of the second distal wire segment 34 is approximately 0.15-0.25 mm. The diameter of the third distal wire segment 36 is approximately 0.10-2 mm.

As shown in the embodiment of FIG. 2, relatively sharp or immediate stepped-down transitions in diameter are provided from the proximal 30 to first 32, first 32 to second 34 and second 34 to third 36 segments. It will be appreciated, that some or all of these points of stepped-down transition may be gradually tapered so as to provide a gradual decrease in diameter rather than the substantially immediate stepped-down diameter shown in FIG. 2a.

An alternative embodiment of the guidewire 10a is shown in FIG. 2a. In such alternative embodiment, the distal portion D of the guidewire 10a comprises a single tapered distal wire segment 33. Such single tapered distal wire segment 33 is preferably formed by machining (i.e., turning down) the distal portion of the proximal wire segment 30a so as to form the single tapered distal wire segment 33. In the embodiment shown in FIG. 2a, the single tapered distal wire segment 33 preferably has an outer diameter at its proximal end equal to that of the proximal wire segment 30a and is gradually tapered to a smaller outer diameter of 0.1-0.2 at its distal end (i.e., immediately adjacent the bulbous distal tip member 46a). An annular shoulder or notch 35 is formed in the single tapered distal wire segment 33 to receive the proximal end of outer coil 40, such that the outer surface of coil 40a is substantially flush with, and forms a smooth transition from the adjacent outer surface of proximal wire segment 30a.

In either embodiment (FIGS. 2 and 2a), the outer coil 40 may be formed of tightly coiled thin stainless steel wire. Preferably the diameter of the wire which forms the coil 40 is approximately equal to the difference between the outer diameter ($OD_1$) of the proximal wire member 30 and the outer diameter ($OD_2$) of the first distal wire core member 32. By such sizing, the outer surface of the coil 40 will be substantially flush with the adjacent outer surface of the proximal wire member 30, as shown.

The outer wire coil 40 and/or the outer surface of the proximal wire member 30 may be coated with pliable coating material such as fluorocarbon coating (e.g., Teflon TM, E. I. Dupont de Neumours, Corp., Wilmington, Del.), silicone coating (e.g., MTX Coating, Dow Corning Corp., Midland, Mich.) or other smooth or lubricious coating material.

The above-described preferred constructions (FIGS. 2. 2a) of the distal portion D of the guidewire body 14 serves to accomplish efficient delivery of ultrasonic vibration to the distal tip 46 of the device 10, while, at the same time, providing for flexibility of the distal portion D, relative to the proximal portion P. The stepped down reductions (FIG. 2) or continuous tapered reduction (FIG. 2a) of the diameter of the distal wire segment(s) 32, 34, and 36, or 33, causes the ultrasound energy being transmitted through the guidewire 10 to undergo to an amplification phenomenon. The preferred relative lengths and constructions of the distal D and proximal P portions of the guidewire 10, 10a serve to minimize the propensity for fracture or breakage of the guidewire as may occur due to localized amplification phenomenon which occurs as the ultrasound energy travels from one diameter wire to a smaller diameter wire.

A blunt or bulbous tip member 46 is formed on or attached to the distal end of the third inner wire member 36 by weldment, mechanical means, or any other suitable means of attachment. The outer coil 40 extends to and preferably abuts against the proximal face of the bulbous tip member 46. In the embodiments shown, the bulbous tip member 46 is formed by melting of the distal portion of the third distal wire member 36 and the surrounding coil member 40 such that the molten material fuses and forms a solid, bulbous distal tip 46. Constant spinning of the device 10 during such melting/fusing process results in formation of a bulbous distal tip member 46 which is substantially round and substantially symmetrical. In alternative embodiments, the bulbous distal tip member 46 may comprise a separate stainless steel ball or other ball member fused or attached to the distal end of the third distal wire segment 36 and/or distal end of the outer coil 40 by way of weldments, adhesive or any other suitable attachment means.

On the extreme proximal end of the proximal wire member 30, there is mounted a proximal connector assembly 18, such as the assembly shown in detail in FIGS. 4 and 5.

With reference to FIGS. 4 and 5, the proximal end connector assembly 18 comprises a sonic connector apparatus having an inner core portion 54 and an outer sleeve portion 56. The proximal end of proximal wire member 30 extends into and is gripped within the bore 58 of the inner core portion 54 of the sonic connector assembly such that ultrasonic vibration may be imparted to proximal wire member 30 through the sonic connector assembly 18.

The inner core portion 54 of the sonic connector 52 has an elongate central bore 58 which extends longitudinally therethrough. The proximal end of the proximal wire member 30 extends through the elongate bore 58 of the inner core member 54, as shown. A proximal region of the bore 58 of inner core member 54 is of increased diameter, slightly larger than the outer diameter of the proximal wire member 30, thereby providing for an annular gap 60 surrounding the proximal most portion of the proximal wire member 30. The remainder of the bore 58 is of substantially the same outer diameter as the proximal wire member 30. When tightened onto the transducer horn H, as shown, the inner core member 54 will become compressed into the slotted foresection of the outer sleeve member 56 causing inward compression of the inner core member 54, thereby frictionally holding and gripping the proximal wire member 30, within its bore 58, thus preventing longitudinal slippage of the proximal wire member 30 from the sonic connector 52.

The horn H of the attendant ultrasound transducer is provided with an externally threaded male portion $H_1$. The sonic connector assembly 52 of the device 10 is internally threaded, as shown to receive and frictionally retain the externally threaded male portion $H_1$ of the transducer horn H. When the externally threaded male portion of H1 of transducer horn H is threadably advanced and received within the sonic connector assembly 52, the proximal extension 53 of the inner core member 54 will be inserted into and operationally coupled to the horn H, such that ultrasound will efficiently pass from the horn H into the sonic connector assembly 52.

By the above-described construction, the proximal connector assembly 18 functions to efficiently connect the ultrasonic guidewire device 10 of the present invention to an ultrasound transducer such that ultrasonic energy may be passed in the distal direction, through the ultrasonic guidewire 10.

It will be appreciated that various other proximal connectors may be utilized for purposes of connecting the guidewire 10 to an ultrasound transducer such that ultrasonic energy will be transmitted from the transducer into the guidewire 10. It is preferable that any such proximal connector assembly utilized in conjunction with this invention be fully removeable from the body of the guidewire 10 such that the guidewire 10 may be readily utilized for passage of catheters, scopes or other instruments thereover.

ii. Preferred Methods of Using the Ultrasonic Guidewire Device of the Present Invention The ultrasonic guidewire 10 of the present invention may be utilized for various purposes including, but not limited to, the specific therapeutic methodologies described in Examples 1 and 2 set forth herebelow.

Example 1

A Method of Using An Ultrasonic Guidewire of The Present Invention In A Percutaneous Transluminal Angioplasty Procedure FIGS. 6a–6g provide a step-wise illustration of a percutaneous transluminal angioplasty procedure wherein an ultrasonic guidewire device 10 of the present invention is utilized, in conjunction with a balloon dilation catheter 100, to open an occlusive lesion OL which totally or near-totally blocks the lumen L of a blood vessel BV.

With reference to FIGS. 6a–6g, the guidewire device 10 is percutaneously inserted, distal end first, into the vasculature. The guidewire device 10 is then advanced to a position whereat the distal tip of the guidewire 10 is adjacent the occlusive lesion OL. A tubular guide catheter 102 is advanced over the pre-positioned guidewire 10 (or may be inserted concomitantly with the guidewire 10) in accordance with standard procedure. In embodiments where the guidewire is formed of radiopaque material, proper placement of the guidewire may be guided and/or verified radiographically.

Ultrasonic energy preferably having a frequency of 18–25 KHz is then passed through the ultrasonic guidewire device 10 causing ultrasonic vibration of the distal tip 46 of the guidewire device 10. The guidewire device 10 is then slowly advanced into the occlusive lesion OL. The ultrasonic vibration of the distal tip 46 of the ultrasonic guidewire device 10 will facilitate passage of the guidewire 10 through the totally or near-totally occlusive lesion OL, thereby creating a longitudinal bore hole or passageway 104 through the occlusive lesion OL (see FIG. 6c–6d).

After the bore hole or passageway 104 has been created by the guidewire 10, the ultrasonic energy is deactuated and the guidewire device 10 may be advanced further in the distal direction to a point where the distal tip 46 has passed well beyond the distal-most extent of the occlusive lesion OL. (e.g. 1–10 mm beyond the lesion)

Thereafter, the balloon dilation catheter 100 (e.g., Slinky ™ PTCA catheter Model 72-SL2-3.0, Baxter Healthcare Corporation, Edwards Less Invasive Surgery Division, Irvine, Calif.) is advanced over the guidewire body 14 to a point where the deflated balloon 106 resides within the bore hole or passageway 104 which has been created within the occlusive lesion OL. Thereafter, the balloon 106 of balloon catheter 100 is inflated so as to radially dilate the occlusive lesion OL (see FIG. 6f).

After one or more inflations of the balloon 106 to effect the desired degree of dilation of the occlusive lesion OL, a quantity of radiographic contrast material may be infused through guide catheter 102 to facilitate radiographic determination of whether an acceptable degree of patency has been restored to the blood vessel BV.

After the restored patency of the blood vessel BV has been confirmed, the guide catheter 102, the balloon catheter 100, and ultrasonic guidewire device 10 may be extracted and removed from the patient's body.

As a result of this procedure, the amount of blood flow through blood vessel BV is significantly improved.

Example 2

A Method Of Using The Ultrasonic Guidewire To Treat Vasospasm

FIGS. 7a–7e provide a step-wise illustration of a method of using the ultrasonic guidewire 10 of the present invention to treat vasospasm in a blood vessel BV.

Vasospasm is known to occur in arteries wherein endovascular interventional procedures (e.g., angioplasty, endarterectomy, etc. . . . ) have been or are being performed. In some blood vessels, such as the coronary arteries, the occurrence of vasospasm constitutes an acute emergency which requires immediate treatment to prevent severe ischemic changes and/or infarction of tissue.

Specific methods by which ultrasonic energy may be utilized to effect vasorelaxation are described in pending U.S. patent application Ser. No. 07/911,651 entitled ANGIOPLASTY AND ABLATIVE DEVICES HAVING ONBOARD ULTRASOUND COMPONENTS AND DEVICES AND METHODS FOR UTILIZING ULTRASOUND TO TREAT VASOSPASM, THE ENTIRETY OF WHICH IS EXPRESSLY INCORPORATED HEREIN BY REFERENCE.

As shown in FIGS. 7a–7e an ultrasound guidewire device 10 of the present invention has been inserted through a guide catheter 102 and has been utilized to facilitate placement of a treatment catheter 100a (e.g., balloon angioplasty catheter, laser ablation catheter, atherectomy device, etc. . . . ). The treatment catheter 100a has been retracted into the lumen of the guide catheter 102 and, following retraction of the treatment catheter 100a, vasospasm has occurred in the blood vessel BV so as to result in near total closure of the lumen L within the region of the blood vessel BV wherein such vasospasm is occurring.

Figure 7A:
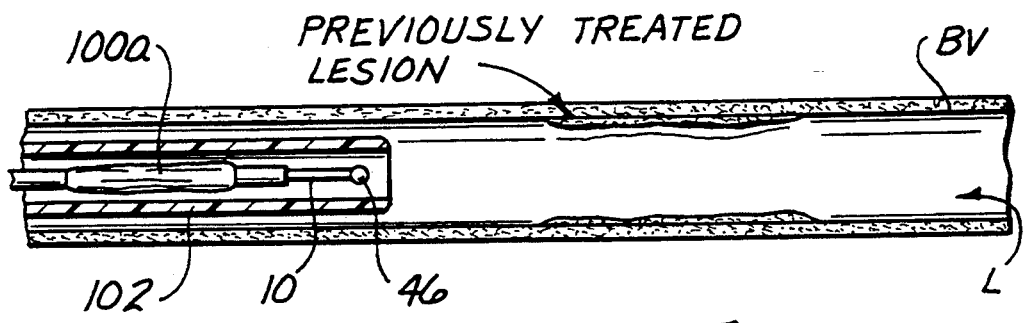
FIG. 7a-e is a step-wise illustration of a procedure wherein the ultrasonic guidewire of the present invention is utilized to treat vasospasm within an artery.
Figure 7B:
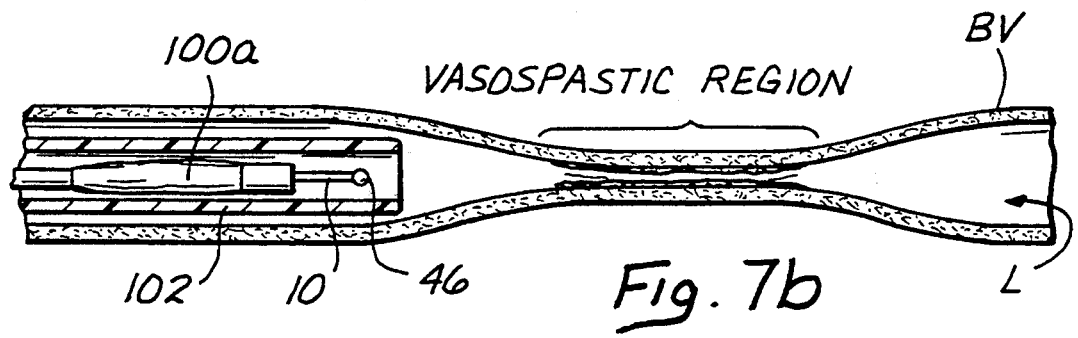
Figure 7C:
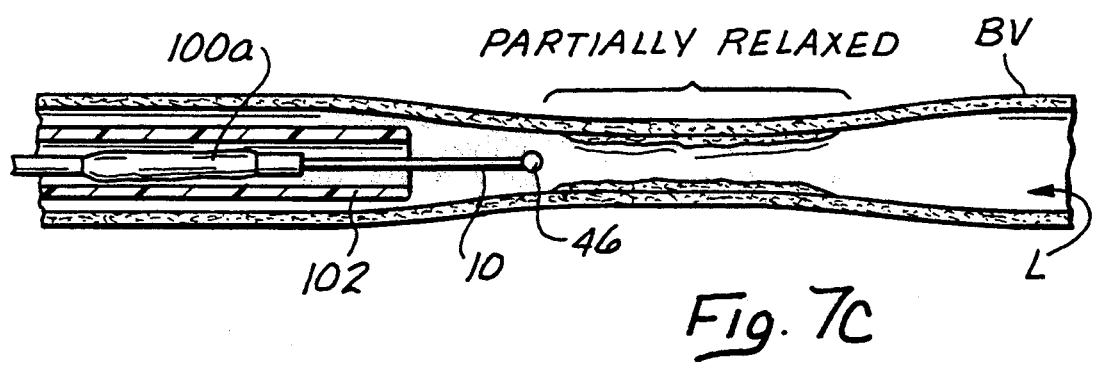
Figure 7D:
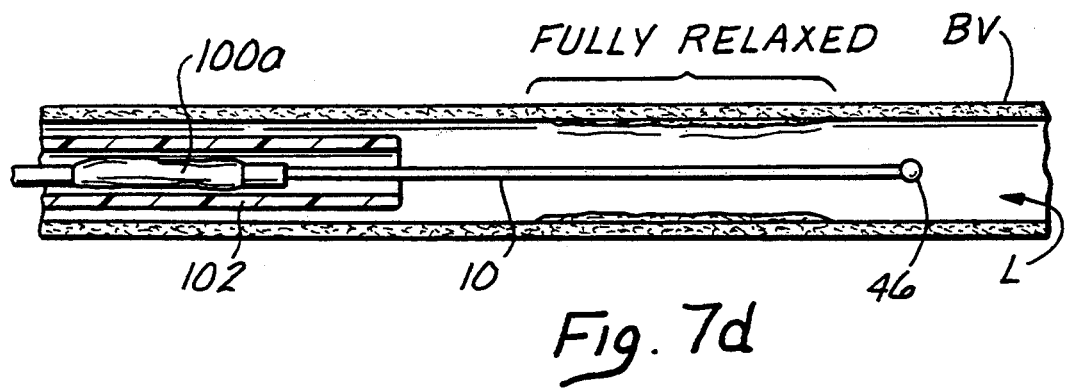
Figure 7E:
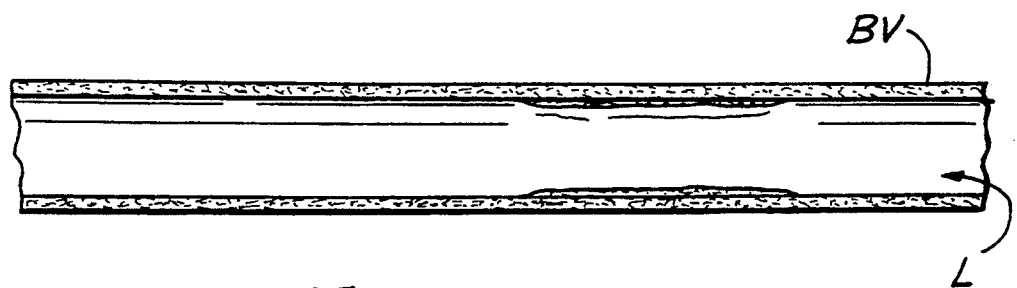

As shown in FIGS. 7c–7e, the vasospasm of the blood vessel BV is treated by passing ultrasonic energy through the ultrasonic guidewire device 10 within a preferred frequency range of 18–25. The ultrasonic guidewire device 10 is slowly advanced in the distal direction, such that the distal tip 46 of the guidewire device 10 passes through the spastic region of the blood vessel BV.

Thereafter, the ultrasonic guidewire device 10 may be slowly moved back and forth such that the distal tip 46 of the guidewire device 10 repeatedly passes through the spastic region of the blood vessel BV.

Exposure of the spastic region of the blood vessel BV to ultrasonic vibration within the frequency range of 18–25 emanating from the ultrasonic guidewire 10 causes the blood vessel BV to relax, thereby reversing the previously observed vasospasm.

After relaxation of the vasospasm has been established, the guide catheter 102, treatment catheter 100a and ultrasonic guidewire device 10 may be extracted and removed.

What is claimed is:

1. An ultrasonic guidewire device comprising:
   a) an elongate guidewire body comprising:
      i) an elongate proximal wire segment having a proximal end and a distal end;
      ii) at least one distal wire segment extending longitudinally from the distal end of said proximal wire segment, said at least one distal wire segment having a cross-sectional dimension which is smaller than the cross-sectional dimension of said elongate proximal wire segment, and wherein the cross-sectional dimensions of the distal wire segments are no greater than 0.3 mm; and
      iii) an outer wire coil helically wound around said at least one distal wire segment; and
   b) a proximal connector apparatus mountable on the proximal end of said guidewire body to couple said guidewire body to an ultrasound source.

2. The ultrasonic guidewire of claim 1 wherein said at least one distal wire segment comprises:
   a first distal wire segment having a proximal end and a distal end, said first distal wire segment extending longitudinally from the distal end of said proximal wire member, said first distal wire segment having a first cross-sectional dimension smaller than the cross-sectional dimension of said proximal wire member;
   a second distal wire segment having a proximal end and a distal end, said second distal wire segment extending longitudinally from the distal end of said first distal wire segment, said second distal wire segment having a second cross-section dimension smaller than the said first cross-section dimension of said first distal wire segment.

3. The ultrasonic guidewire of claim 2 wherein said at least one distal wire segment further comprises:
   a third distal wire segment having a proximal end and a distal end, said third distal wire segment extending longitudinally from the distal end of said second distal wire segment, said third distal wire segment having a third cross-sectional dimension smaller than the said second cross-sectional dimension of said second distal wire segment.

4. The ultrasonic guidewire of claim 2 wherein there exists a sharp non-tapered transition from the cross-sectional dimension of said proximal wire member to the first cross-sectional dimension of said first distal wire segment.

5. The ultrasonic guidewire of claim 2 wherein there exists a gradual-tapered transition from the cross-sectional dimension of said proximal wire member to the first cross-sectional dimension of said first distal wire segment.

6. The ultrasonic guidewire of claim 2 wherein there exists a sharp non-tapered transition from the first cross-sectional dimension of said first distal wire segment and the second cross-sectional dimension of said second distal wire segment.

7. The ultrasonic guidewire of claim 2 wherein there exists a gradual-tapered transition from the first cross-sectional dimension of said first distal wire segment and the second cross-sectional dimension of said second distal wire segment.

8. The ultrasonic guidewire of claim 3 wherein there exists a sharp non-tapered transition from the second cross-sectional dimension of said second distal wire segment and the third cross-sectional dimension of said third distal wire segment.

9. The ultrasonic guidewire of claim 3 wherein there exists a gradual-tapered transition from the second cross-sectional dimension of said second distal wire segment and the third cross-sectional dimension of said third distal wire segment.

10. The ultrasonic guidewire of claim 1 wherein said at least one distal wire segment comprises:
    a single tapered distal wire segment having a proximal and a distal end, said single tapered distal wire segment extending longitudinally from the distal end of said proximal wire segment having a gradually reduced cross-sectional dimension such that the cross-sectional dimension at the distal end of said single tapered distal wire segment smaller than the cross-sectional dimension of said proximal wire segment.

11. The ultrasonic guidewire of claim 1 wherein said outer wire coil is of substantially continuous diameter.

12. The ultrasonic guidewire of claim 1 further comprising a blunt distal tip member on the distal end of said guidewire body.

13. The ultrasonic guidewire of claim 12 wherein the distal-most portions of said at least one distal wire segment and said surrounding outer coil are melted together to comprise said blunt distal tip member.

14. The ultrasonic guidewire of claim 1 wherein said elongate proximal wire member is 20–150 cm. in length.

15. The ultrasonic guidewire of claim 1 wherein said at least one distal wire segment is 1–40 cm. in length.

16. The ultrasonic guidewire of claim 15 wherein said outer wire coil is 1–40 cm. in length and substantially coextensive with said at least one distal wire segment.

17. The ultrasonic guidewire of claim 1 wherein said proximal connector apparatus is removable from the proximal end of said guidewire.

18. The ultrasonic guidewire of claim 1 wherein said proximal connector apparatus comprises a connector member tightenable on the proximal end of said guidewire body so as to grippingly attach to the proximal end of said guidewire body, said connector member having a threaded distal portion thereon, said distal portion being threadably engageable with a separate ultrasound source.

19. The ultrasonic guidewire of claim 1 further in combination with an ultrasound source, said ultrasound source comprising:
   an electrical signal generator; and
   an ultrasound transducer coupled to said electrical signal generator;
   said ultrasound transducer being operative to convert an electrical signal received from said signal generator into ultrasonic energy.

20. The ultrasonic guidewire of claim 1 wherein the elongate guidewire body is made from a nickel-titanium alloy.

21. A method for percutaneous transluminal treatment of an obstruction in an anatomical passageway to improve the patency of said anatomical passageway, said method comprising the steps of:
   a) providing a treatment apparatus which is transluminally advanceable through said passageway and which is operable to effect patency improving treatment of said obstruction;
   b) providing an ultrasonic guidewire having a proximal end and a distal end, said guidewire being coupleable to an ultrasound generating device such that ultrasonic energy from said ultrasound generating device will pass through said ultrasonic guidewire to the distal end thereof, said guidewire further comprising:
      (i) at least one distal wire segment extending longitudinally from the distal end of said proximal wire segment, said at least one distal wire segment having a cross-sectional diameter which is smaller than the cross-sectional diameter of said proximal wire segment, and wherein the cross-sectional diameters of the distal wire segments are no greater than 0.3 mm; and
      (ii) an outer wire coil helically wound around said at least one distal wire segment;
   c) providing an ultrasound generating device coupleable to said ultrasonic guidewire;
   d) inserting said ultrasonic guidewire, distal end first, into said anatomical passageway;
   e) advancing said ultrasonic guidewire to a point where the distal end of said ultrasonic guidewire is near said obstruction;
   f) utilizing said ultrasound generating device to pass ultrasonic energy through said ultrasonic guidewire while concommitantly advancing the distal end of said guidewire through said obstruction so as to create a passageway through said obstruction;
   g) subsequently advancing said treatment apparatus over said guidewire and into the passageway created through said obstruction; and
   h) utilizing said treatment apparatus to effect patency improving treatment of said obstruction.

22. The method of claim 21 wherein said passageway is a blood vessel and wherein said obstruction is atherosclerotic plaque.

23. The method of claim 21 wherein said passageway is a blood vessel and wherein said obstruction is thrombus.

24. The method of claim 21 wherein said treatment device comprises a balloon angioplasty catheter and wherein step (h) further comprises:
   positioning the balloon of said balloon angioplasty catheter within the passageway created by said ultrasonic guidewire; and
   utilizing said balloon angioplasty catheter to dilate said obstruction.

* * * * *